United States Patent [19]

Bláha et al.

[11] Patent Number: 4,847,403
[45] Date of Patent: Jul. 11, 1989

[54] 2-ISOPROPYL-2-(2-METHYLPHENYL)-5-(N-METHYL-N-HOMOVERATRYLAMINO)-VALERONITRILE AND METHOD FOR PRODUCING SAME

[75] Inventors: Luedvík Bláha; Miroslav Rajšner; Ivan Helfert; Václav Trčka, all of Praha, Czechoslovakia

[73] Assignee: Spofa, spojene podniky pro zdravotnickou, Praha, Czechoslovakia

[21] Appl. No.: 74,801

[22] Filed: Jul. 17, 1987

[30] Foreign Application Priority Data

Jul. 18, 1986 [CS] Czechoslovakia .................. 5462-86

[51] Int. Cl.$^4$ ............................................. C07D 317/60
[52] U.S. Cl. ..................................... 558/390; 558/359
[58] Field of Search ............................. 558/390, 359

[56] References Cited

U.S. PATENT DOCUMENTS 4,350,636 9/1982 Kastner et al. .................... 558/390

FOREIGN PATENT DOCUMENTS 1154810 4/1964 Fed. Rep. of Germany .

OTHER PUBLICATIONS

B. N. Singh et al., Drugs 15, 169–97, 1978, "Verapamil: A Review of its Pharmacological Properties and Therapeutic Use".
R. Mannhold et al., Arch. Pharmacol. 302, 217–226, 1978 Investigations on the Structure–Activity Relationships of Verapamil.
H. D. Hoeltje, Arch. Pharmazie 315, 317–23, 1982 "Theoretische Untersuchung zu Struktur–Wirkungsbeziehungen von ringsubstituier-ten Verapamil-Derivaten".

Primary Examiner—H. M. S. Sneed
Assistant Examiner—Chung K. Pak
Attorney, Agent, or Firm—Klein & Vibber

[57] ABSTRACT

2-Isopropyl-2-(2-methylphenyl)-5-(N-methyl-homoveratrylamino)-valeronitrile ("mepamil") of the Formula I:

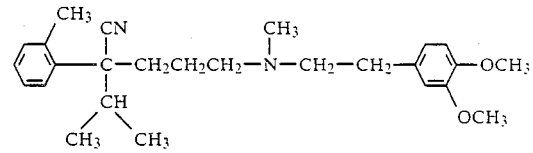

preferably administered in the form of water-soluble acid addition salts such as e.g. hydrochloride. The claimed compound is advantageously prepared by alkylation of 2-(2-methylphenyl)-3-methylbutyronitrile with 3,3-diethoxypropylchloride. Subsequently, the obtained 5,5-diethoxy-2-isopropyl-2-(2-Methylphenyl)-valeronitrile is mildly, acidically hydrolisized to yield the appropriate aldehyde, i.e. 2-isopropyl-2-(2-methylphenyl)-5-oxovaleronitrile. This aldehyde is then reacted with N-methylhomoveratrylamine under conditions of reductive alkylation, suitably by catalytic hydrogenation over a platinum or palladium catalyst or by chemical reduction with the use of formic acid as a reducing agent. The resulting base is optionally converted by neutralization with a pharmaceutically acceptable organic or inorganic acid, i.e. hydrochloric or fumaric acid, into the corresponding acid addition salt.

8 Claims, No Drawings

2-ISOPROPYL-2-(2-METHYLPHENYL)-5-(N-METHYL-N-HOMOVERATRYLAMINO)-VALERONITRILE AND METHOD FOR PRODUCING SAME

FIELD OF THE INVENTION

The invention relates to 2-isopropyl-2-(2-methylphenyl)-5-(N-methyl-N-homoveratrylamino)-valeronitrile of Formula I:

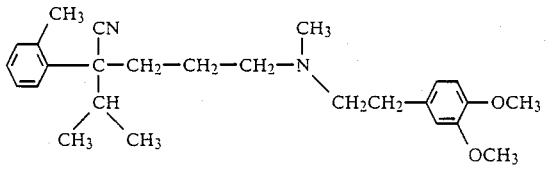

and its addition salts with pharmaceutically acceptable inorganic or organic acids, and a method for producing same.

DESCRIPTION OF PRIOR ARTS

The pertinent prior art literature describes numerous valeronitrile derivatives of generally related chemical structure. From among these known compounds is the most relevant compound, 2-(3,4-dimethoxyphenyl)-2-isopropyl-5-(N-methyl-N-homoveratrylamino)-valeronitrile (hereinafter "verapamil", which is the nonproprietary name of the relevant known prior art). Such compound is in clinical use for the treatment of coronary heart disease, certain cardiac arrhythmias and recently also hypertension.

SUMMARY OF THE ADVANTAGES OF THE PRESENT INVENTION AND DETAILED DESCRIPTION OF ITS PREFERRED USE

Quite unexpectedly it was found that the herein claimed valeronitrile derivative, ie. 2-isopropyl-2-(2-methylphenyl)-5-(N-methyl-N-homoveratrylamino)-valeronitrile (hereinafter "mepamil" which is the yet non-proprietary name given to the compound claimed herein), which is clearly distinguished from the known structures by the fact that the methyl substituent on the benzene nucleus is attached in the position ortho with regard to the aliphatic connecting chain, and is thus substantially less toxic than the afore-named known compound ("verapamil"). The compound of the present invention ("mepamil"), which is preferably administered in the form of water-soluble acid addition salts such as e.g. hydrochloride, possesses useful pharmacodynamic properties, more particularly it evidences significant calcium-antagonistic and cardiac antiarrhythmic activity.

Biological properties of the subject compounds were evaluated both on isolated animal organs, and in vivo in experimental animals. Thus, for instance, the antiarrhythmic, negative inotropic (diminishing the heart contractility) and calcium ions blocking effects were tested on isolated electrically stimulated rabbit hearts atria by determining respectively the prolongation of the functional refractory period, the decrease of heart contractility and the blocked of calcium-induced heart contractions dependently on rising concentration of the compounds under test in the nutrient medium of the organ tissue culture. The calcium ions blocking effect was also evaluated by determining the degree of inhibition of calcium-induced contractions of isolated rabbit aortas. In vivo tests of the antiarrhythmic activity were performed in rats on experimental model arrhythmias induced by i.v. administration of aconitin, acetylcholine or calcium chloride. In almost all of these tests mepamil elicited beneficial effects comparable to those of verapamil used as a structurally related reference compound.

Mepamil elicits a markedly pronounced calcium ions blocking effect on isolated rabbit atrias; also its calcium-antagonistic action on isolated smooth muscle of blood vessel wall is significant. The corresponding $ED_{50}$ values on rabbit atria and aortas are respectively $4 \times 10^{-3}$ and $9.3 \times 10^{-3}$ umole/ml. On isolated rabbit atria mepamil elicits prolongation of the functional refractory period and has a favorably lower negative inotropic effect as compared to verapamil; the respective $ED_{50}$ values of the two agents are $1.2 \times 10^{-2}$ and $3.6 \times 10^{-3}$ umole/ml. Mepamil has antiarrhythmic properties in experimentally induced arrhythmias both in vitro (e.g. on isolated rabbit atria) and in vivo, in experimental animals. Thus, it blocks barium chloride arrhythmia in rabbits, lowers the incidence of arrhythmias on i.v. administration of aconitin in rats and efficiently suppresses heart rhythm disturbances in the same animals on rapid i.v. injection of acetylcholine. It also prevents fibrilation of heart ventriculi on i.v. administration of calcium chloride.

In hemodynamic studies in dogs and monkeys mepamil both on oral and i.v. administration lowers the systolic and especially the diastolic blood pressure, substantially reduces the heart rat and increases the blood flow rate in arteria carotis and particularly in coronary sinus. It increases the cardiac output and simultaneously diminishes the peripheral vascular resistance. Thus, in experiments in anesthetized dogs mepamil doses ranging from 0.45 to 4.5 mg/kg i.v. reduce the systolic and diastolic blood pressure (respectively by up to 15 and 50%) as well as the heart rate (by up to 30%). Verapamil in similar doses elicits somewhat more pronounced effects, but when administered in doses of above 1 mg/kg i.v. it markedly lowers the myocardial contractility and induces atrioventricular block. In dogs mepamil dose of 0.45 mg/kg i.v. substantially increases the blood flow rate in coronary sinus (by as much as 90% for a short time period). In conscious Macaca mulatta (Rhesus) monkeys an oral dose of 45 mg/kg of mepamil has a mild hypotensive effect in animals with increased initial blood pressure level. Intravenously a dose of 4.5 mg/kg of the agent induces a short decrease both in systolic and diastolic blood pressure and lowers the heart rate in monkeys. Also in DOCA-hypertensive rats a dose of 45 Mg/kg p.o. of mepamil has a significant hypotensive effect.

Changes in left ventricular pressure in dogs versus time curve derivation confirm that mepamil has only a slight negative inotropic effect; this on the contrary is adversely high in verapamil.

The in vitro carcinogenity test of mepamil was negative, i.e. no signs of carcinogenic properties were observed. No mutagenic effect on Salmonella typhi murium was detectable.

In the short-time toxicity test in mice mepamil is five times less toxic on i.v. administration and twice less toxic on oral ingestion as compared to verapamil. Thus, $LD_{50}$ of mepamil is 28 mg/kg intravenously and 620 mg/kg orally. On the other hand $LD_{50}$ of verapamil is 5 mg/kg i.v.. During the four-week toxicity test in rats the administration of mepamil in daily doses of 25 and 100 mg/kg p.o. QD (on each day) elicited no significant differences in growth curves or adverse biochemical or histological changes in comparison with the control group animals.

The above summarized pharmacological assay results show that mepamil can find therapeutic use in similar medical indications as verapamil, i.e. especially in the treatment of coronary heart disease and certain arrhythmias, while at the same time allowing for higher safety because of substantially lower incidence of undesired side effects in the course of therapy in view of the reported slight toxicity and significantly diminished negative inotropic effect of the claimed compound.

For the purpose of therapeutic use, the active claimed compound can be formulated into convenient medicinal dosage forms such as e.g. tablets, coated tablets, capsules, injections, spray or transdermally acting plasters by known means.

The aforementioned claimed compound is advantageously prepared by alkylation of 2-(2-methylphenyl)-3-methylbutyronitrile, which is a known compound described in the literature (see. W. Herz, J.Am.Chem.-Soc. 80, 3139, 1958), with 3,3-diethoxypropylchloride, subsequent mild acidic hydrolysis of the obtained 5,5-diethoxy-2-isopropyl-2-(2-methylphenyl)valeronitrile to yield the appropriate aldehyde, i.e. 2-isopropyl-2-(2-methylphenyl)-5-oxovaleronitrile, and reaction of this aldehyde with N-methyl-homoveratrylamine under conditions of reductive alkylation, suitably by catalytic hydrogenation over a platinum or palladium catalyst or by chemical reduction with the use of formic acid as the reducing agent. The resulting base is optionally converted by neutralization with a pharmaceutically acceptable inorganic or organic acid into the corresponding acid addition salt.

The alkylation of 2-(2-methylphenyl)-3-methylbutyronitrile of Formula II:

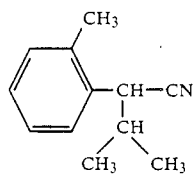

with 3,3-diethoxypropylchloride is carried out conveniently in an inert organic solvent in the presence of an alkaline condensing agent. Suitable inert organic solvents are aromatic hydrocarbons, e.g. benzene, toluene or commercial xylene, tertiary amides, e.g. dimethylformamide, or higher-boiling aliphatic ethers, e.g. ethyleneglycol dimethylether. Preferable alkaline condensing agent is sodium hydride or sodium amide. The reaction is advantageously effected by dropping a toluenic sodium amide suspension to a boiling solution of the above reactants in anhydrous toluene and refluxing the mixture for a period of 4 to 10 hours. The so formed acetal, 5,5-diethoxy-2-isopropyl-2-(2-methylphenyl) valeronitrile of Formula III:

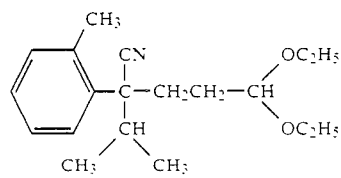

is isolated on cooling the mixture by short agitation with water, separation of the toluenic phase and evaporation of the solvent. The obtained crude product is purified by distillation under reduced pressure.

In the subsequent reaction step the resulting acetal is subjected to mild acidically catalyzed hydrolysis to yield the corresponding aldehyde, 2-isopropyl-2-(2-methylphenyl)-5-oxovaleronitrile of Formula IV:

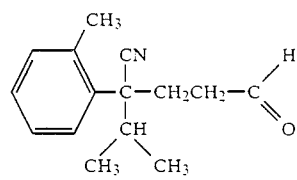

This hydrolysis can be conducted in aqueous acetone or wet ether in the presence of an inorganic, e.g. sulfuric or hydrochloric, or organic, e.g. p-toluenesulfonic, trifluoroacetic or oxalic acid, conveniently at a temperature not exceeding 50° C., and requires a period of approx. 2 to 10 hours. Preferable procedure consists in refluxing a stirred mixture of equimolar quantities of the above acetal and oxalic acid dihydrate in acetone to a temperature of 30° to 40° C. for a period of 3 to 5 hours. The liberated aldehyde is isolated by neutralization of the oxalic acid with an aqueous potassium carbonate solution, separation of the potassium oxalate precipitate, evaporation of the solvent, short stirring of the residue with water and a suitable water-immiscible solvent, e.g. ether, separation of the organic phase and removal of the solvent.

The obtained crude aldehyde of Formula IV can be used immediately, without separate additional purification, for the final stage of the synthesis, reductive alkylation of the commercially available N-methyl-homoveratrylamine under the formation of the desired valeronitrile derivative of Formula I. This reductive alkylation can be effected either by hydrogenation of a solution of these reactants in a $C_1$ to $C_4$ alcanol over platinum dioxide or palladium on a suitable carrier substrate, e.g. active carbon, at a temperature of 20° to 40° C., or by chemical reduction with the use of formic acid as the reducing agent in an appropriate inert organic solvent, e.g. benzene, toluene, a $C_1$ to $C_4$ alcanol, chloroform, ethyl acetate or aqueous dimethylformamide, at a temperature ranging from approx. 20° C. to the boiling temperature of the reaction mixture. Advantageous procedure consists in refluxing a mixture of the aldehyde, N-methylhomoveratrylamine and 90% formic acid in toluene until the evolution of carbon dioxide is complete. The desired final product is isolated on cooling the reaction mixture by extraction into dilute sulfuric or hydrochloric acid, subsequent alkalization of the separated aqueous phase e.g. with a sodium hydroxide solution, extraction of the liberated oily base into a suitable water-immiscible organic solvent, e.g. benzene, toluene, ether, chloroform or dichloromethane, and removal of the solvent. The obtained base of Formula I can be converted by neutralization with appropriate inorganic or organic acids, e.g. hydrochloric or fumaric acid, into the corresponding acid additions salts.

Starting materials required for the preparation are known substances available by methods described in the pertinent prior art literature.

EXAMPLES OF PREFERRED EMBODIMENTS

Further particulars of the procedure are illustrated by the subsequent non-limitative examples:

Example 1

5,5-Diethoxy-2-isopropyl-2-(2-methylphenyl)-valeronitrile

To a boiling solution of 2-(2-methylphenyl)-3-methylbutyronitrile (Herz W., J.Am.Chem.Soc. 80, 3139, 1958) (207.9 g) and 86% 3,3-diethoxypropylchloride (154 g) in anhydrous toluene (1250 ml) is dropped during about 50 minutes under stirring 107.7 g of a 50% toluenic sodium amide suspension ($NaNH_2$ content 53.8 g) and the mixture is refluxed under continuous stirring for 6 hours. On subsequent cooling, the stirred mixture is diluted with water (300 ml), the toluenic portion is separated and the aqueous phase is extracted with toluene. The organic solutions are combined, washed with water and saturated brine (aqueous sodium chloride solution) until the reaction is neutral, and then it is dried over anhydrous sodium sulfate. Finally, the solvent is evaporated under reduced pressure and the residue is distilled to give 302.9 g (83.2%) of 5,5-diethoxy-2-isopropyl-2-(2-methylphenyl-valeronitrile, b.p. 102° to 104° C. at 4 Pa.

Example 2

2-(2-Methylphenyl)-2-isopropyl-5-oxovaleronitrile

To a solution of 5,5-diethoxy-2-isopropyl-2-(2-methylphenyl)-valeronitrile (267 g) in acetone (2000 ml) is added under stirring a solution of oxalic acid dihydrate (121.7 g) in water (730 ml) and the mixture is warmed under continuous stirring for 4 hours at 40° C. Thereafter it is cooled and under external cooling to 520 C. adjusted by the addition of a 50% aqueous potassium carbonate solution to pH within the range of 6 to 6.5. The formed potassium oxalate precipitate is filtered off and washed with acetone (500 ml). From the filtrate the solvent is evaporated under reduced pressure (bath temperature above 30° C.). The residue is mixed with water (600 ml) and ether (500 ml), the separated aqueous phase is extracted with ether (2×300 ml), the combined organic solutions are washed with aqueous sodium hydrogencarbonate, water and staturated brine until neutral reaction, dried over anhydrous magnesium sulfate and the solvent is evaporated (bath temperature about 30° C.) under reduced pressure, finally at about 1.3 kPa, to yield 203 g of the oily crude product (claimed compound content of 93.2% as determined by gas-liquid chromatography). The obtained material is used without separate purification for the subsequent reductive alkylation.

Example 3

2-Isopropyl-2-(2-methylphenyl)-5-(N-methyl-homoveratrylamino)-valeronitrile

Procedure A

A mixture of crude 2-isopropyl-2-(2-methylphenyl)-5-oxovaleronitrile (6.9 g, content 93.2%), N-methyl-homoveratrylamine (5.9 g), platinum dioxide (0.1 g) and methanol (150 ml) is shaken in a hydrogenation vessel under under hydrogen until discontinuation of the gas absorption (for about 40 minutes). Platinum metal formed by reduction of the oxide is separated, washed with methanol and the solvent is evaporated from the filtrate under reduced pressure. The residue is mixed with water (120 ml), and ether (90 ml), the mixture is acidified with dilute hydrochloric acid, the separated aqueous phase is then extracted with ether and alkalized with a 4% sodium hydroxide solution. The liberated oily base is extracted into ether, the extract is then washed with water and saturated brine, and dried over anhydrous sodium sulfate, and the solvent is finally evaporated to give 11.2 g (91.4%) of the oily base. The obtained product is dissolved in a mixture of ether (30) ml) and 2-propanol (5 ml), and the solution is acidified with an etheric hydrogen chloride solution to yield crystalline hydrochloride, m.p. 159° to 161° C. (from 2-propanol).

Procedure B

A mixture of 2-isopropyl-2-(2-methylphenyl)-5-oxovaleronitrile (201.8 g, content 93%), N-methyl-homoveratrylamine (159.8 g), 90% formic acid (44.25 g) and toluene (1200 ml) is slowly warmed under stirring to the boiling temperature and gently boiled under reflux until discontinuation of the evolution of carbon dioxide (for about 1 hour). On cooling the reaction mixture the product is extracted into dilute hydrochloric acid and water, the combined acidic aqueous solutions are washed with ether and alkalized with aqueous sodium hydroxide solution. The liberated oily base is extracted into ether, the extract is then washed with water and saturated brine, dried over anhydrous sodium sulfate, and ether is finally evaporated to give the oily product (293 g, 87.4%). Similarly as described in the preceding paragraph for procedure A, the obtained base is converted into the hydrochloride (313 g, 85.7%) melting at 154° to 158° C. on recrystallization from 2-propanol pure hydrochloride, and has a m.p. of 159° to 161° C.

I claim:

1. A method for producing 2-Isopropyl-2-(2-methylphenyl)-5-(N-methylhomoveratrylamino-valeronitrile and acid addition salts thereof of Formula I:

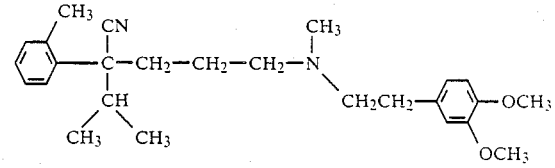

comprising the steps of:
alkylating 2-(2-methylphenyl)-3-methylbutyronitrile of Formula II:

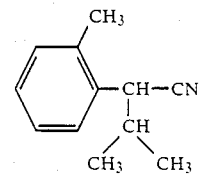

with 3,3-diethoxypropylchloride in an inert organic solvent in the presence of an alkaline condensing agent to form 5-diethoxy-2-isopropyl-2-(2- methylphenyl)5,5-diethoxy-2-isopropyl-2-(2-methylphenyl)-valeronitrile of Formula III:

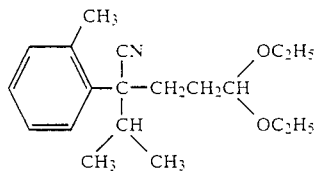

hydrolyzing the said compound of Formula III to yield an aldehyde (2-isopropyl-2-(2-methylphenyl)-5-oxovaleronitrile), of Formula IV:

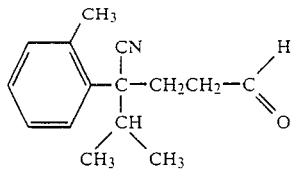

reacting said compound of Formula IV with N-methylhomoveratrylamine under reductive alkylation conditions, to form the oily base of the compound of Formula I;

isolating and converting said oily base into purified form of the compound of formula I by neutralization with a pharmaceutically acceptable acid.

2. The method as described in claim 1 wherein the inert organic solvents are selected from the group consisting of aromatic hydrocarbons, tertiary amides, and high-boiling aliphatic ethers, and the alkaline condensing agent is sodium hydride or sodium amide.

3. The method as described in claim 2 wherein, during the alkylizing step, the method comprises the additional steps of
adding a sodium amide suspension in anhydrous toluene to the boiling alkalizing solution of Formula II and 3,3-diethoxypropylchloride;
refluxing the mixture for a period of 4 to 10 hours to result in the compound of Formula III;
isolating the compound of Formula III by cooling the mixture by way of short agitation with water;
separating the toluenic phase;
evaporating the toluene solvent to obtain a crude product of Formula III; and
purifying the crude product of Formula III by distillation under reduced pressure.

4. The method as described in claim 1 wherein the hydrolysis is conducted in aqueous acetone or anhydrous ether in acid medium at a temperature not exceeding 50° C., for 2 to 10 hours to yield the aldehyde of Formula IV.

5. The method as described in claim 3 wherein the hydrolysis is conducted in aqueous acetone in the presence of an oxalic acid dihydrate, to a temperature of 30° to 40° C. for a time period of 3 to 5 hours to yield an aldehyde of the Formula IV.

6. The method as described in claim 5 wherein the aldehyde of the Formula IV is isolated by
neutralizing the oxalic acid with an aqueous potassium carbonate solution;
separating the potassium oxalate precipitate;
evaporating the solvent;
stirring of the residue with water and a water-immiscible solvent;
separating the organic phase; and
removing the solvent.

7. The method as described in claim 6 wherein the reductive alkylation is conducted in a $C_1$ to $C_4$ alkanol over platinum dioxide or palladium on a carrier substrate at a temperature of 20° to 40° C.; or by chemical reduction with the use of formic acid as the reducing agent in an inert organic solvent selected from the group consisting of a $C_1$ to $C_4$ alkanol, chloroform, ethyl acetate and aqueous dimethylformamide, at a temperature ranging from 20° C. to the boiling temperature of the reaction mixture while
refluxing in 90% formic acid in toluene until the evolution of carbon dioxide is complete to form the compound of formula I; then
isolating the compound of formula I on cooling the reaction mixture by extraction with dilute acid; and subsequently
alkalizing the resulting separated aqueous phase;
extracting the liberated oily base of the compound of formula I with a water-immiscible organic solvent;
removing the solvent;
converting this oily base of formula I into a corresponding acid addition salt by neutralization with a pharmaceutically acceptable inorganic or organic acid.

8. A combinative method for producing the compound having formula I:

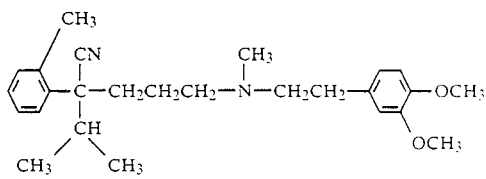

comprising the steps of:
alkylating 2-(2-methylphenyl)-3-methylbutyronitrile of Formula II

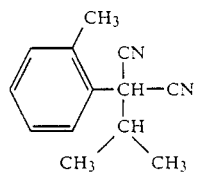

with 3,3-diethoxypropylchloride in an inert organic solvent in the presence of an alkaline condensing agent; bringing the resulting solution to a boil;
adding a sodium amide suspension in anhydrous toluene to the boiling solution of the compound of Formula II and 3,3-diethoxypropylchloride;
refluxing the resulting mixture for a period of 4 to 10 hours to form the compound of Formula III;

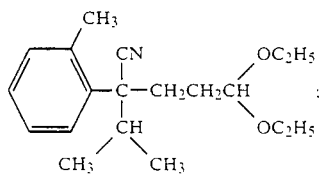

isolating the compound of Formula III in the mixture by cooling said mixture with water;
separating the resulting toluene containing phase;
evaporating the toluene solvent from the toluene containing phase to obtain a crude product of Formula III; and
purifying said crude product of Formula III in an aqueous solvent in the presence of an acid, at a temperature not exceeding 50° C., for 2 to 10 hours to yield an aldehyde of the Formula IV;

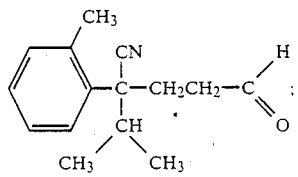

isolating said aldehyde of Formula IV by neutralizing said acid with an aqueous potassium carbonate solution;
separating the resulting precipitate;
stirring the precipitate with water and a water-immiscible solvent;
separating the resulting organic phase;
removing the solvent from the organic phase;
reacting the resulting isolated compound of Formula IV with N-methyl-homoveratrylamine under reductive alkylating conditions to form the compound of Formula I, wherein the reductive alkylation is conducted in a $C_1$ to $C_4$ alkanol over platinum dioxide or palladium on a carrier substrate at a temperature of 20° to 40° C.; or by chemical reduction with the use of formic acid as the reducing agent in an inert organic solvent at a temperature ranging from 20° C. to the boiling temperature of the reaction mixture; while
refluxing in 90% formic acid in toluene until the evolution of carbon dioxide is complete to form the compound of formula I then;
isolating the compound of Formula I by cooling the reaction mixture by extraction with dilute acid; and subsequently
alkalizing the resulting separated aqueous phase;
extracting the liberated oily base of the compound of Formula I with a water-immiscible organic solvent;
removing said solvent; and,
converting said compound of Formula I into a corresponding acid salt by neutralization with a pharmaceutically acceptable acid.

* * * * *